US00PP15351P2

(12) United States Plant Patent
Smith

(10) Patent No.: US PP15,351 P2
(45) Date of Patent: Nov. 23, 2004

(54) *CHRYSANTHEMUM* PLANT NAMED 'FOXY YONATASHA'

(50) Latin Name: *Chrysanthemum×morifolium*
Varietal Denomination: Foxy Yonatasha

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/764,882

(22) Filed: Jan. 26, 2004

(51) Int. Cl.[7] ..... A01H 5/00
(52) U.S. Cl. ..... Plt./298
(58) Field of Search ..... Plt./298

*Primary Examiner*—Anne Marie Grünberg
(74) *Attorney, Agent, or Firm*—C. A. Whealy

(57) ABSTRACT

A new and distinct cultivar of *Chrysanthemum* plant named 'Foxy Yonatasha', characterized by its upright and outwardly spreading plant habit; freely branching habit; dense and full plant habit; uniform and very freely flowering habit; large daisy-type inflorescences with elongated oblong-shaped ray florets; red-colored ray florets and bright yellow-colored disc florets; and natural season flowering in mid September in the Northern Hemisphere.

2 Drawing Sheets

Botanical classification/cultivar designation: *Chrysanthemum×morifolium* cultivar Foxy Yonatasha.

BACKGROUND OF THE INVENTION

The present invention relates to a new and distinct cultivar of *Chrysanthemum* plant, botanically known as *Chrysanthemum×morifolium*, commercially known as a garden-type *Chrysanthemum* and hereinafter referred to by the name 'Foxy Yonatasha'.

The new *Chrysanthemum* is a naturally-occurring whole plant mutation of the *Chrysanthemum×morifolium* cultivar Yonatasha, disclosed in U.S. Plant Pat. No. 13,907. The new *Chrysanthemum* was discovered and selected by the Inventor as a single flowering plant from within a population of plants of the cultivar Yonatasha in a controlled environment in Alva, Fla. in April, 2002. The selection of this plant was based on its desirable inflorescence form, attractive ray floret color and good garden performance.

Asexual reproduction of the new cultivar by terminal vegetative cuttings in a controlled environment in Alva, Fla. since June, 2002, has shown that the unique features of this new *Chrysanthemum* are stable and reproduced true to type in successive generations.

SUMMARY OF THE INVENTION

The cultivar Foxy Yonatasha has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Foxy Yonatasha'. These characteristics in combination distinguish 'Foxy Yonatasha' as a new and distinct cultivar:

1. Upright and outwardly spreading plant habit.
2. Freely branching habit; dense and full plants.
3. Uniform and very freely flowering habit.
4. Large daisy-type inflorescences with elongated oblong-shaped ray florets.
5. Red-colored ray florets and bright yellow-colored disc florets.

6. Natural season flowering in mid September in the Northern Hemisphere.

In side-by-side comparisons conducted in Alva, Fla., plants of the new *Chrysanthemum* differed from plants of the parent, the cultivar Yonatasha in the following characteristics:

1. Plants of the new *Chrysanthemum* flowered several days later than plants of the cultivar Yonatasha when grown under natural season conditions.
2. Plants of the new *Chrysanthemum* and the cultivar Yonatasha differed in ray floret coloration as plants of the cultivar Yonatasha had coral pink-colored ray florets.

Plants of the new *Chrysanthemum* can be compared to plants of the *Chrysanthemum* cultivar Hot Salsa, disclosed in U.S. Plant Pat. No. 11,918. In side-by-side comparisons conducted in Alva, Fla., plants of the new *Chrysanthemum* differed from plants of the cultivar Hot Salsa in the following characteristics:

1. Plants of the new *Chrysanthemum* were larger and more rounded than plants of the cultivar Hot Salsa.
2. Plants of the new *Chrysanthemum* flowered about three weeks earlier than plants of the cultivar Hot Salsa when grown in southern climates.
3. Ray florets of plants of the new *Chrysanthemum* were darker red in color than ray florets of plants of the cultivar Hot Salsa.

Plants of the new *Chrysanthemum* can also be compared to plants of the *Chrysanthemum* cultivar Red Temptress, not patented. In side-by-side comparisons conducted in Alva, Fla., plants of the new *Chrysanthemum* differed from plants of the cultivar Red Temptress in the following characteristics:

1. Plants of the new *Chrysanthemum* were smaller and more rounded than plants of the cultivar Red Temptress.
2. Plants of the new *Chrysanthemum* had larger inflorescences than plants of the cultivar Red Temptress.
3. Plants of the new *Chrysanthemum* flowered about four weeks earlier than plants of the cultivar Red Temptress when grown in southern climates.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plant of 'Foxy Yonatasha' grown in a container.

The photograph on the second sheet comprises a close-up view of typical inflorescences of the cultivar 'Foxy Yonatasha'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Alva, Fla. during the winter in a fiberglass-covered greenhouse under conditions and practices which approximate those generally used in commercial garden-type *Chrysanthemum* production. One cutting was planted in a 15.25-cm container in early December, 2002. Plants were pinched one time, that is, the terminal apex was removed to enhance branching, at the end of December. One week after the pinch, plants were exposed to short day/long night photoperiodic treatments until flowering. During the production of the plants, day temperatures averaged 26° C. and night averaged 18° C. Measurements and numerical values represent averages for typical flowering plants.

Botanical classification: *Chrysanthemum×morifolium* cultivar Foxy Yonatasha.

Commercial classification: Daisy-type garden *Chrysanthemum*.

Parentage: Naturally-occurring whole plant mutation of the *Chrysanthemum×morifolium* cultivar Yonatasha, disclosed in U.S. Plant Pat. No. 13,907.

Propagation:

*Type*.—Terminal vegetative cuttings.

*Time to initiate roots*.—About four days at 21° C.

*Time to produce a rooted cutting*.—About ten to twelve days at 21° C.

*Root description*.—Fine, fibrous; white in color.

*Rooting habit*.—Freely branching.

Plant description:

*Plant form/growth habit*.—Perennial herbaceous daisy-type garden *Chrysanthemum*. Inverted triangle with mounded crown. Stems initially upright, then outwardly spreading. Freely branching with about ten lateral branches per plant. Moderately vigorous to vigorous.

*Plant height*.—About 17 cm.

*Plant diameter*.—About 28 cm.

*Lateral branches*.—Length: About 15.5 cm. Diameter: About 2 mm. Internode length: About 1 cm. Aspect: Upright and outwardly spreading. Texture: Pubescent. Color: 146A.

*Foliage description*.—Leaf arrangement: Alternate. Length: About 5.4 cm. Width: About 3.9 cm. Apex: Mucronate. Base: Truncate. Margin: Palmately lobed, sinuses divergent to parallel. Texture, upper surface: Slightly pubescent. Texture, lower surface: Pubescent; veins prominent. Color: Developing foliage, upper surface: Slightly darker than 147A. Developing foliage, lower surface: 147B. Fully expanded foliage, upper surface: 147A. Fully expanded foliage, lower surface: 147B. Venation, upper surface: 147A. Venation, lower surface: Close to 147B. Petiole length: About 1.8 cm. Petiole diameter: About 1.75 mm. Petiole color, upper surface: 147A to 147B. Petiole color, lower surface: 147B.

Inflorescence description:

*Appearance*.—Daisy-type inflorescence form with elongated oblong-shaped ray florets. Inflorescences borne on terminals above foliage, arising from leaf axils. Disc and ray florets developing acropetally on a capitulum. Very freely flowering with about 32 inflorescences per lateral branch.

*Flowering response*.—Under natural season conditions, plants flower in mid September in the Northern Hemisphere.

*Inflorescence bud* (*before showing color*).—Height: About 4.5 mm. Diameter: About 6 mm. Shape: Oblate. Color (lower surface of phyllaries): Darker than 146A to close to 147A.

*Inflorescence size*.—Diameter: Large, about 5 cm. Depth (height): About 1 cm. Disc diameter: About 1.3 cm. Receptacle diameter: About 3.5 mm.

*Ray florets*.—Shape: Elongated oblong, narrow. Length: About 2.5 cm. Corolla tube length: About 2.5 mm. Width: About 5 mm. Apex: Emarginate. Base: Fused. Margin: Entire. Texture: Smooth, glabrous; velvety. Surface: Flat to reflexed. Orientation: Initially upright, then perpendicular to vertical. Number of ray florets per inflorescence: About 26 in a single whorl. Color: When opening and fully opened, upper surface: 6A overlain with 53A to 59A; color becoming closer to 185B with development. When opening and fully opened, lower surface: Close to 6D underlain with close to 59A.

*Disc florets*.—Shape: Tubular; apex dentate, five-pointed. Length: About 5 mm. Width, apex: About 2 mm. Width, base: About 1 mm. Number of disc florets per inflorescence: About 102. Color: Immature: Close to 154A to 9A. Mature: Apex: Close to 9A. Mid-section: Close to 144B. Base: Close to 155D.

*Phyllaries*.—Quantity per inflorescence: About 16. Length: About 6 mm. Width: About 3 mm. Shape: Lanceolate. Apex: Acute. Base: Truncate. Margin: Entire. Texture, upper surface: Smooth, waxy. Texture, lower surface: Pubescent. Color, upper surface: Close to 147A. Color, lower surface: Darker than 146A to close to 147A.

*Peduncle*.—Length: First peduncle: About 4.5 cm. Fourth peduncle: About 6.6 cm. Seventh peduncle: About 10.4 cm. Diameter: About 1.5 mm. Strength: Strong. Aspect: About 40° from vertical. Texture: Pubescent. Color: 144A.

*Reproductive organs*.—Androecium: Present on disc florets only. Anther color: 9A. Pollen: None observed. Gynoecium: Present on both ray and disc florets.

*Seed/fruit*.—Seed and fruit production has not been observed.

Disease/pest resistance: Plants of the new *Chrysanthemum* have not been shown to be resistant to pathogens and pests common to *Chrysanthemums*.

Garden performance: Plants of the new *Chrysanthemum* have been observed to be tolerant to rain, wind and temperatures ranging from 0 to more than 38° C.

It is claimed:

1. A new and distinct cultivar of *Chrysanthemum* plant named 'Foxy Yonatasha', as illustrated and described.

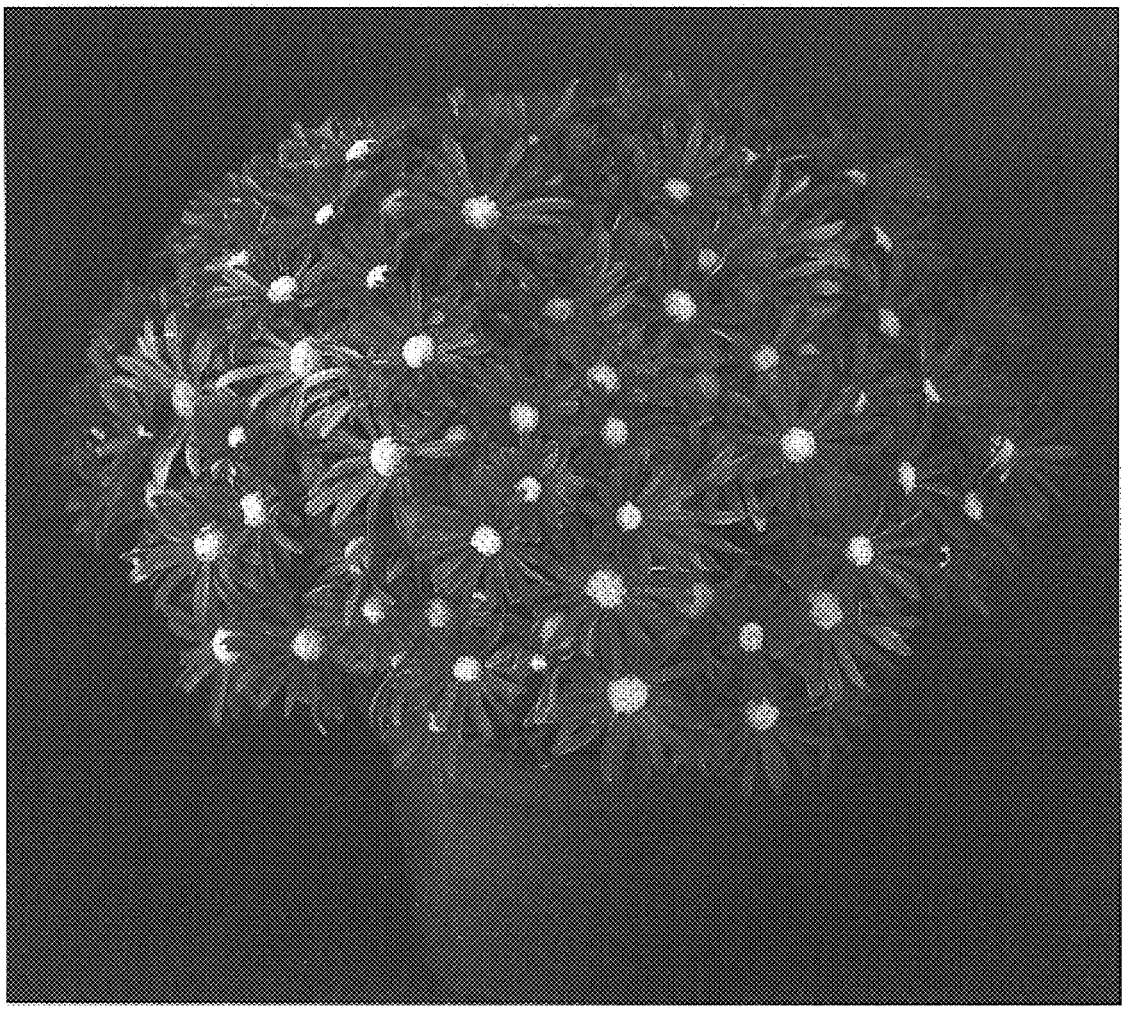

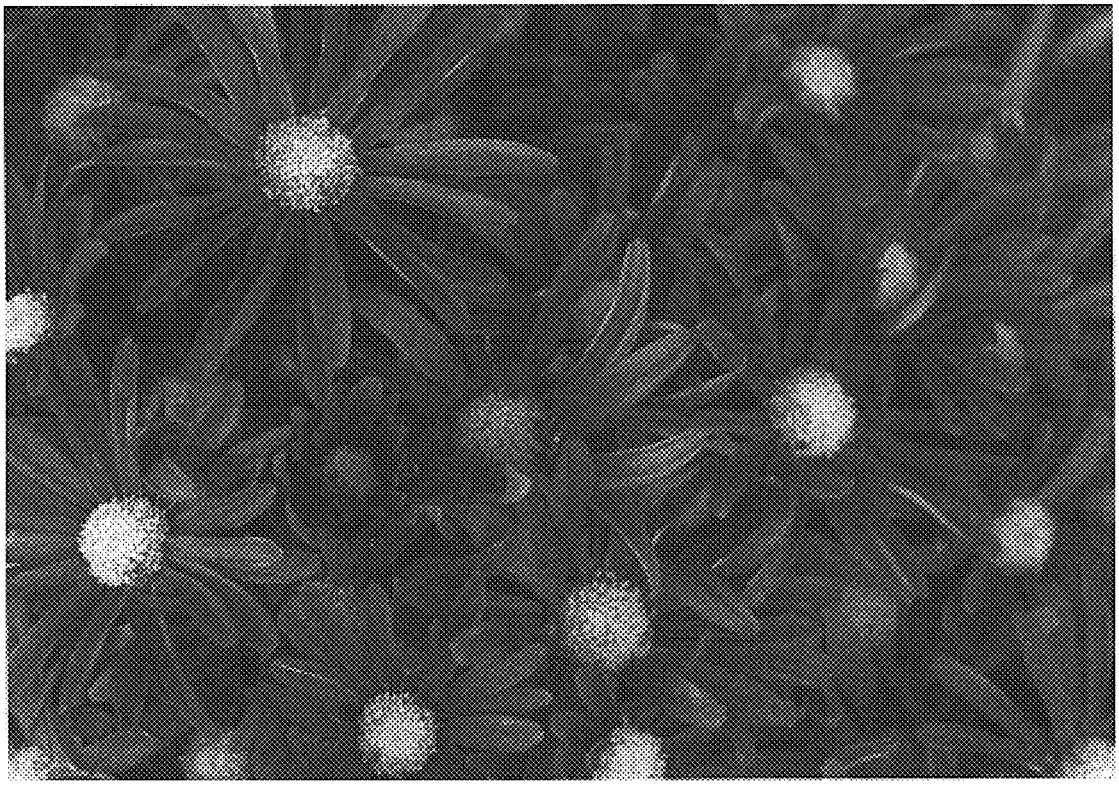

* * * * *